United States Patent [19]

Hausmann et al.

[11] Patent Number: 4,626,274
[45] Date of Patent: Dec. 2, 1986

[54] HERBICIDAL AGENTS

[75] Inventors: Heinz Hausmann, Leichlingen; Robert R. Schmidt, Bergisch-Gladbach; Herbert Voege, Leverkusen, all of Fed. Rep. of Germany

[73] Assignee: Bayer Aktiengesellschaft, Leverkusen, Fed. Rep. of Germany

[21] Appl. No.: 557,685

[22] Filed: Dec. 2, 1983

[30] Foreign Application Priority Data

Dec. 20, 1982 [DE] Fed. Rep. of Germany ....... 3247050

[51] Int. Cl.⁴ ............................................. A01N 25/30
[52] U.S. Cl. ......................................... 71/93; 71/106; 71/90; 71/79; 71/DIG. 1
[58] Field of Search ...................... 71/DIG. 1, 106, 93

[56] References Cited

U.S. PATENT DOCUMENTS

| | | | |
|---|---|---|---|
| 2,841,483 | 7/1953 | Swezey et al. | 71/122 |
| 3,619,165 | 11/1971 | Covey et al. | 71/106 |
| 3,619,168 | 11/1971 | Mecklenborg et al. | 71/106 |
| 3,948,635 | 4/1976 | Vachette et al. | 71/92 |
| 3,997,322 | 12/1976 | Ratledge | 71/93 |
| 4,182,621 | 1/1980 | Ogata et al. | 71/76 |

FOREIGN PATENT DOCUMENTS

| | | |
|---|---|---|
| 0022666 | 1/1981 | European Pat. Off. |
| 2614841 | 10/1977 | Fed. Rep. of Germany . |
| 1234225 | 6/1971 | United Kingdom . |
| 1255249 | 12/1971 | United Kingdom . |
| 2052260 | 1/1981 | United Kingdom . |
| 2057265 | 4/1981 | United Kingdom . |

OTHER PUBLICATIONS

Hellingman et al., Chem. Abst. vol. 72 (1970) 120344y.
Japanese Koki 76 12,929, Chem. Abst. vol. 85 (1976) 73438p.
Chemical Abstracts, vol. 83, No. 21, 11/24/75 (3 pages)p,173771.
Journal of Plant Diseases and Protection 87 (5/6), 335–345, 1980 Interaction of Different Lipid Components with Various Fungicides.

*Primary Examiner*—Catherine L. Mills
*Attorney, Agent, or Firm*—Sprung Horn Kramer & Woods

[57] ABSTRACT

A known herbicide such as a urea, carboxylic acid ester, aminoacid, benzoic acid derivative, benzonitrile, phenol derivative, diphenyl ether, carbamate, phenoxyalkanecarboxylic acid, triazine, triazinone, triazinedione, heterocycle, dipyridil derivative or benzosulphonamide, is rendered more effective by being combined with a synthetic spreading agent such as a silicone oil, fatty acid ester or fatty alcohol, e.g. isopropyl myristate, metamitron, ametridion or methabenzthiazuran.

8 Claims, No Drawings

HERBICIDAL AGENTS

The invention relates to new herbicidal synergistic substance combinations which contain, in addition to a known herbicide, a known synthetic spreading agent and can advantageously be used in combating weeds.

It is already known that the addition of relatively large amounts of spreading agents to formulations, for example in pharmacy, leads to an improvement in absorption (compare U.S. Pat. No. 4,096,262).

It is also already known that the addition of surface-active substances to pesticidal formulations in amounts above the content required to reduce the surface tensions of aqueous spray liquors and which optionally contain other auxiliaries, can lead to increases in action (compare European Pat. No. 22,666).

It is also known that, for example, triazines, such as, for example, 1-amino-3-(2,2-dimethylpropyl)-6-ethylthio-1,3,5-triazine-2,4-(1H,3H)-dione, can be used as herbicides (compare, for example, Danish patent specification No. 136,067).

It has now been found, surprisingly, that the new substance combinations which contain 0.01 to 10 parts by weight of a herbicide per part by weight of spreading agent have a particularly powerful herbicidal action.

Surprisingly, the activity of the substance combinations according to the invention is substantially more powerful than the sum of the actions of the individual substances, the spreading agent having a negligible intrinsic action or none at all. There is an unforeseeable true synergistic effect, and not merely an additive effect.

This increase in action by the addition of known compounds which are inactive in plant protection is particularly important, since the active - compound concentration is thereby reduced, with an equally good result, and pollution of the environment is therefore reduced. The easy handling of such substance combinations is furthermore to be emphasized, it being possible to use the formulations as a tank mix, that is to say the herbicide is suspended in water at the location and the commercially available spreading agent, to which an emulsifier is added, is mixed in. The mixture can be applied directly, which means no stability problems and the like arise, which is a further advantage. On the other hand, the active compounds and spreading agent can also be processed to finished formulations in a manner which is in itself known.

The new substance combinations are thus a valuable enrichment in the context of combating weeds.

By herbicides there are to be understood, in the present case, ureas, carboxylic acid esters, aminoacids, benzoic acid derivatives, benzonitriles, phenol derivatives, diphenyl ethers, carbamates, phenoxyalkanecarboxylic acids, s-triazines, as-triazinones, heterocyclic compounds, s-triazinediones, dipyridine derivatives and benzosulphonamides which are suitable for combating weeds.

Examples which may be mentioned of ureas having a herbicidal action are, for example:

1. (1) N'-(3-chloro-4-methylphenyl)-N,N-dimethylurea (chlortoluron), (2) N'-(4-isopropylphenyl)-N,N-dimethylurea (isoproturon), (3) N'-(3,4-dichlorophenyl)-N-methoxy-N-methylurea (linuron), (4) N-benzothiazol-2-yl-N-methyl-N'-methyl-urea (methabenzthiazuron) and (5) N'-(3-chloro-4-methoxyphenyl)-N,N-dimethylurea (metoxuron).

Examples which may be mentioned of carboxylic acid esters having a herbicidal action are, for example:

2. (1) ethyl N-benzoyl-N-3,4-dichlorophenyl)-2-aminopropionate (benzoylprop-ethyl), (2) methyl 2-chloro-3-(4-chlorophenyl)-propionate (chlorfenprop-methyl), (3) methyl 2-[4-(2,4-dichlorophenoxy)-phenox]-propionate (diclofop-methyl), (4) methyl N-benzoyl-N-(3-chloro-4-fluorophenyl)-2-aminopropionate (flamprop-methyl), (5) isopropyl N-benzoyl-(3-chloro-4-fluoro-phenyl)-2-aminopropionate (flamprop-isopropyl), (6) methyl or ethoxyethyl 2-[4-(3-chloro-5-trifluoromethyl-2-pyridinyloxy)-phenoxy-]-propionate (Dowco 453), (7) butyl 2-[4-(5-trifluoromethyl)-2-pyridinyloxy-phenoxy]-propionate (fluazifop-butyl), (8) 2- [4-(6-chloro-2-benzothiazolyloxy)-phenoxy]-propionic acid and esters thereof (fenthiaprop), (9) 2-[4-(6-chloro-benzoxazolyl-oxy)-phenoxy]-propionic acid and esters thereof (fenoxaprop), (10) 2-(benzyloxy)-ethyl 2 -[4-(3,5-dichloro-pyrid-2-yloxy)-phenoxy]-propionate and (11) trimethylsilyl-methyl 2-[4-(3,5-dichloro-pyrid-2-yloxy)-phenoxy]-propionate.

Examples which may be mentioned of aminoacids having a herbicidal action are, for example:

3. (1) N-phosphonomethylglycine (glyphosat) and (2) 2-amino-4-hydroxy-methylphosphinyl-butanoic acid (glufosinat).

An example which may be mentioned of a benzoic acid derivative having a herbicidal action is, for example:

4. (1) 2-methoxy-3,6-dichloro-benzoic acid (dicamba).

Examples which may be mentioned of benzonitriles having a herbicidal action are, for example:

5. (1) 3,5-diiodo-4-hydroxy-benzonitrile (ioxynil) and (2) 3,5-diiodo-4-hydroxy-benzonitrile (bromoxynil).

Examples which may be mentioned of phenol derivatives having a herbicidal action are, for example:

6. (1) 2-methyl-4,6-dinitrophenol DNOC), (2) 2,4-dinitro-6-tert.-butylphenol (dinoterb) and (3) 2-sec.-butyl-4,6-dinitrophenyl acetate (dinoseb-acetate).

Examples which may be mentioned of diphenyl ethers having a herbicidal action are, for example:

7. (1) 2,4-dichlorophenyl 4-nitrophenyl ether (nitrofen), (2) 5-(2-chloro-4-trifluoromethylphenoxy)-2-nitrobenzoic acid (acifluorfen), (3) ethoxycarbonyl-methyl 2-[3-(2,6-dichloro-4-trifluoromethyl-phenoxy)-6-nitrophenoxy]-propionate and (4) ethoxymethyl 2-[3-(2-chloro-4-trifluoromethyl-phenoxy)-6-nitro-phenoxy]-propionate.

An example which may be mentioned of a carbamate having a herbicidal action is, for example:

8. (1) 3-methoxycarbonylaminophenyl N-3'-methylphenyl)-carbamate (phenmedipham).

Examples which may be mentioned of phenoxyalkanecarboxylic acids having a herbicidal action are, for example:

9. (1) 2,4-dichlorophenoxyacetic acid (2,4-D), (2) 2,4-dichlorophenoxypropionic acid (2,4-DP), (3) 4-chloro-2-methylphenoxyacetic acid (MCPA) and (4) 2-(2-methyl-4-chlorophenoxy)-propionic acid (MCPP, mecoprop).

Examples which may be mentioned of s-triazines having a herbicidal action are, for example:

10. (1) 2-chloro-4-ethylamino-6-(1-methyl-1-cyanoethylamino)-s-triazine (cyanazine), (2) 2-chloro-4,6-bis(ethylamino)-s-triazine (simazine), (3) 2-ethylamino-4-methylthio-6-tert.-butylamino-s-triazine (terbutryn) and (4) 2-chloro-4-ethylamino-6-isopropylamino-s-triazine (atrazine).

Examples which may be mentioned of as-triazin-5-ones having a herbicidal action are, for example:

11. (1) 4-isobutylidene amino-6-tert.-butyl-3-(methylthio)-as-triazin-5-(4H)-one (isome-thiozin), (2) 4-amino-6-tert.-butyl-3-(methylthio)-as-triazin-5(4H)-one (metribuzin), (3) 4-amino-3-methyl-6-phenyl-as-triazin-5(4H)-one (metamitron) and (4) 4-amino-6-tert.-butyl-3-(ethylthio)-as-triazin-5(4H)-one.

Examples which may be mentioned of heterocyclic active compounds having herbicidal action are, for example:

12. (1) 3-isopropyl-2,1,3-benzo-thiadiazin-4-one 2,2-dioxide (bentazon) and (2) 1,2-dimethyl-3,5-diphenyl-pyrazolium methyl-sulphate (difenzoquat).

Examples which may be mentioned of s-triazinediones having a herbicidal action are, for example:

13. (1) 3-cyclohexyl-6-dimethylamino-1-methyl-1H-s-triazine-2,4-dione (hexazione) and (2) 1-amino-3-(2,2-dimethylpropyl)-6-ethylthio-s-triazine-2,4-dione (ametridione).

Examples which may be mentioned of dipyridils having a herbicidal action are, for example:

14. (1) diquat and (2) paraquat.

An example which may be mentioned of a sulphonamide having a herbicidal action is, for example:

15. (1) 2-chloro-N-[-4-methoxy-6-methyl-1,3,5-triazin-2-yl)-amino]-carbonylbenzenesulphonamide (chlorsulphuron).

By synthetic spreading agents there are to be understood, in the present case, for example, suitable silicone oils, fatty acid esters or fatty alcohols. Examples which may be mentioned are:

16. (1) silicone oils of different viscosities.

Examples of fatty acid esters which may be mentioned are, for example:

17. (1) ethyl stearate, (2) di-n-butyl adipate, (3) hexyl laurate, (4) dipropylene glycol pelargonate, (5) esters of a branched fatty acid of medium chain length and saturated $C_{16}$-$C_{18}$-fatty alcohols, (6) isopropyl myristate, (7) isopropyl palmitate, (8) caprylic/capric acid esters of saturated fatty alcohols of $C_{12}$-$C_{18}$ chain lengths, (9) isopropyl stearate, (10) oleyl oleate, (11) decyl oleate, (12) ethyl oleate, (13) ethyl lactate, (14) dibutyl phthalate and (15) diisopropyl adipate, related ester mixtures and the like.

Examples of fatty alcohols which may be mentioned are, for example:

18. (1) isotridecyl alcohol, (2) 2-octyldodecanol, (3) cetyl-stearyl alcohol and (4) oleyl alcohol.

The following are particularly preferred: isopropyl myristate 17.(6) and isopropyl palmitate 17.(7).

By weeds, in the broadest sense, there are to be understood all plants which grow in locations where they are undesired.

The substance combinations according to the invention are suitable, depending on the concentration, for the total combating of weeds, for example on industrial terrain and rail tracks, and on paths and squares with or without tree plantings. Equally, the combinations can be employed, for example, for combating weeds in perennial cultures, for example afforestations, decorative tree plants, orchards, vineyards, citrus groves, nut orchards, banana plantations, coffee plantations, tea plantations, rubber plantations, oil palm plantations, cocoa plantations, soft fruit plantings and hopfields, and for the selective combating of weeds.

The increased active effect of the substance combination according to the invention is particularly highly pronounced in certain concentration ratios. However, the weight ratios of the components in the combinations can be varied within relatively wide limits. In general, 0.01 to 10 parts by weight of a herbicide, preferably 0.05 to 7.5 parts by weight of a herbicide, are present per part by weight of spreading agent.

The substance combinations can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the substances with liquid solvents and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-dispersed silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsuphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of substance combination, preferably between 0.5 and 90%.

The combinations according to the invention can be used in the form of finished formulations. However, the substances contained in the combinations can also be mixed as individual formulations when used, that is to say they can be used in the form of tank mixes.

The new combinations, as such or in the form of their formulations, can furthermore also be used as mixtures with other known herbicides, finished formulations or tank mixes again being possible. Mixtures with other known active compounds, such as fungicides, insecticides, acaricides, nematicides, bird repellents, plant nutrients and agents which improve soil structure, are also possible.

The new combinations can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, dusting or scattering.

The amounts used of the substance combination according to the invention can be varied within a certain range; they depend, inter alia, on the weather and on soil factors. In general, the amounts used are between 0.005 and 20 kg of active compound combination per ha, preferably between 0.01 and 10 kg/ha.

The substance combinations according to the invention can be applied either before or after emergence of the plants. They can also be incorporated into the soil before sowing.

The increased herbicidal action of the new substance combinations can be seen from the examples which follow. While the individual substances show weaknesses in herbicidal action, the combinations show a very broad action on weeds, which exceeds a simple additive action.

A synergistic effect exists with herbicides whenever the herbicidal action of the active compound combination is greater than that of the individually applied substances.

The action to be expected for a given combination of two substances can (compare Colby, S.R., "Calculating synergistic and antagonistic responses of herbicide combination", Weeds 15, pages 20–22, 1967) be calculated as follows:

If $X = \%$ damage by herbicide A used in an amount of p kg/ha and $Y = \%$ damage by spreading agent B used in an amount of q kg/ha and $E =$ the expected damage by substances A and B used in amounts of p and q kg/ha then $$B = X + Y - \frac{X \cdot Y}{100}.$$

If the actual damage is greater than calculated, the action of the combination is superadditive, that is to say a synergistic effect exists.

The examples which follow show that the found herbicidal action of the substance combination according to the invention on weeds is greater than the calculated action, that is to say the new substance combination has a synergistic action.

EXAMPLE

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 liters of water/ha. After three weeks, the degree of damage to the plants is rated in % damage in comparison to the development of the untreated control. The figures denote:

0% = no action (like untreated control)
100% = total destruction

TABLE A

| Active compound or substance combinations | Amount applied kg/ha | Sugar beet found* | Sugar beet calc.* | Polygonum found* | Polygonum calc.* |
|---|---|---|---|---|---|
| Isopropyl myristate (IPM) [17.(6)] (known) | 5 | 0 | | 0 | |
| Metamitron [11.(3)] (known) | 3 | 0 | | 65 | |
| IPM [17.(6)] + [11.(3)] (according to the invention) | 5 + 3 | 0 | 0 | 100 | 65 |

TABLE B

| Active compound or active compound combination | Amount applied kg/ha | Wheat found* | Wheat calc.* | Galium found* | Galium calc.* |
|---|---|---|---|---|---|
| Isopropyl myristate (IPM) [17.(6)] (known) | 2 | 0 | | 0 | |
| [13.(2)] Ametridion (known) | 1.4 | 0 | | 50 | |
| [17.(6)] + [13 (2)] (according to the invention) | 2 + 1.4 | 0 | 0 | 70 | 50 | found* = action found in percent
calc.* = action calculated according to the Colby formula, in percent

TABLE C

| Active compound or active compound combinations | Amount applied kg/ha | Wheat found* | Wheat calc.* | Galium found* | Galium calc.* |
|---|---|---|---|---|---|
| Isopropyl myristate (IPM) [17.(6)] (known) | 3.5 | 0 | | 0 | |
| [10.(4)] Methabenzthiazuron (known) | 2 | 0 | | 30 | |
| [17.(6)] + [10.4)] (according to the invention) | 3.5 + 2 | 0 | 0 | 90 | 30 | found* = action found in percent
calc.* = action calculated according to the Colby formula, in percent It will be understood that the specification and examples are illustrative but not limitative of the present invention and that other embodiments within the spirit and scope of the invention will suggest themselves to those skilled in the art.

What is claimed is:

1. A herbicidal composition comprising a herbicidally effective amount of a triazine, traizinone or triazinedione herbicide and a synergizing amount of isopropyl myristate as a synthetic spreading agent.

2. A composition according to claim 1, wherein the weight ratio of synthetic spreading agent to herbicidally active compound is between about 1:0.01 and 1:10.

3. A composition according to claim 1, wherein the weight ratio of synthetic spreading agent to herbicidally active compound is between about 1:0.05 and 1:7.5.

4. A composition according to claim 1, wherein the herbicidally active compound is a urea, carboxylic acid ester, aminoacid, benzoic acid derivative, benzonitrile, phenol derivative, diphenyl ether, carbamate, phenoxyalkanecarboxylic acid, triazine, triazinone, triazinedione, heterocycle, dipyridil derivative or benzosulphonamide.

5. A composition according to claim 1, wherein the herbicide is metamitron.

6. A composition according to claim 1, wherein the herbicide is ametridion.

7. A composition according to claim 1, wherein the herbicide is methabenzthiazuron.

8. A method of combating weeds which comprises applying to the weeds or to a field in which the weeds might appear a herbicidally effective amount of a composition according to claim 1.

* * * * *